United States Patent [19]

Zocchi

[11] Patent Number: 5,681,801
[45] Date of Patent: Oct. 28, 1997

[54] STABLE PARTICLE SUSPENDED COMPOSITION

[75] Inventor: Germaine Zocchi, Belgique, Belgium

[73] Assignee: Colgate-Palmolive Company, New York, N.Y.

[21] Appl. No.: 622,513

[22] Filed: Mar. 25, 1996

Related U.S. Application Data

[63] Continuation-in-part of Ser. No. 422,471, Apr. 17, 1995, abandoned.

[51] Int. Cl.$^6$ .................. C11D 1/65; C11D 3/14; A61K 6/00
[52] U.S. Cl. .................. 510/125; 510/119; 510/121; 510/130; 510/139; 510/159; 510/418; 510/470; 514/846; 424/401; 424/70.21; 424/70.24
[58] Field of Search .................. 510/119, 121, 510/125, 130, 159, 418, 139, 470; 514/846; 424/401, 70.21, 70.24

[56] References Cited

U.S. PATENT DOCUMENTS

| | | | |
|---|---|---|---|
| 4,126,674 | 11/1978 | Mausner | 424/31 |
| 4,788,006 | 11/1988 | Bolich, Jr. et al. | 252/550 |
| 4,933,176 | 6/1990 | Van Reeth | 424/70 |
| 5,057,241 | 10/1991 | Merritt et al. | 252/174.17 |
| 5,073,274 | 12/1991 | Caswell | 252/8.6 |
| 5,439,682 | 8/1995 | Wivell et al. | 724/401 |
| 5,449,763 | 9/1995 | Wulff et al. | 536/18.6 |
| 5,518,647 | 5/1996 | Zocchi | 252/174.17 |
| 5,534,265 | 7/1996 | Fowler | 424/489 |
| 5,536,332 | 7/1996 | Chun | 132/202 |
| 5,540,853 | 7/1996 | Trinh et al. | 501/101 |

FOREIGN PATENT DOCUMENTS 0468721  1/1992  European Pat. Off. .

*Primary Examiner*—Paul Lieberman
*Assistant Examiner*—Lorna M. Douyon
*Attorney, Agent, or Firm*—Martin Barancik

[57] ABSTRACT

A combination cleansing, conditioning composition comprising a stable, clear, aqueous cleansing phase having stably dispersed and suspended therein particles bearing the conditioning agent, the aqueous cleansing phase comprising:

a. a high foaming anionic surfactant, b. an amphoteric surfactant in quantities of at least 0.2 wt. % of the composition wherein clarity of the aqueous phase is maintained, c. an effective amount of a viscoelasticity enhancing suspending material comprised of a xantham gum having an initial transmittance in a 1 wt. % distilled water solution of at least 85% as measured by a UV spectrophotometer at 600 nm, and d. the said particles, insoluble and stably suspended in the aqueous phase, bearing an effective amount of oily water insoluble or essentially water insoluble skin or hair conditioning agents, the particles being such a size and material to readily deliver the conditioning agent to the skin or hair when the particle is abraded against the skin or hair during ordinary cleansing activities.

14 Claims, No Drawings

5,681,801

STABLE PARTICLE SUSPENDED COMPOSITION

This application is a continuation-in-part of application Ser. No. 08/422,471 filed on Apr. 17, 1995 now abandoned.

BACKGROUND OF THE INVENTION

There exists a continuing need for preparing cleansing products which perform the proper cleansing, are mild to the skin, condition the skin and are aesthetically pleasing as well. Recently, there have been a number of "2 in 1" products which have attempted to provide these functions in one product. However, these products have a number of disadvantages. For example, the products are marketed as a heavy emulsion which has a tendency to separate in time and is not aesthetically pleasing. Additionally, such systems may have beads which are not stable at long term thereby liberating their contents or are systems wherein the emollient carrying materials are not stably suspended over time and/or the aqueous phase becomes turbid and change color over time. The delivery system of the conditioning agent is not optimized for the efficient deposition of the sensory conditioning agent(s) as well.

A new composition has been discovered which provides a clear, stable single aqueous cleansing phase having stably dispersed and suspended therein particles bearing the conditioning agents. When rubbed on the skin, the particles release the conditioning agents onto the skin in an efficient, productive manner. The clarity of the aqueous cleaning phase and the stability of the conditioner carrying phase maintain their respected clarity and stability for at least three months at 43° C.

SUMMARY OF THE INVENTION

In accordance with the invention, there is a combination cleansing, conditioning composition comprising a stable, clear aqueous cleansing phase having stably dispersed and suspended therein particles bearing the conditioning agents, the said aqueous cleansing phase comprising:

a. A high foaming anionic surfactant, b. An amphoteric surfactant in quantities wherein clarity of the aqueous phase is maintained, c. An effective amount of a viscoelastic enhancing, suspending material comprised of a xanthan gum having an initial transparency prior to addition to the aqueous composition of at least 85%, and d. particles both insoluble and stably suspended in the aqueous phase, bearing an effective amount of an oily, water insoluble or essentially water insoluble skin or hair conditioning agents, the particle being of such a size and material to readily deliver the conditioning agent to the skin or hair when the particle is abraded against the skin or hair during ordinary cleansing activities.

DETAILED DESCRIPTION OF THE INVENTION

Any high foaming anionic surfactant can be employed in the composition. Examples of such surfactants include but are not limited to long chain alkyl (8–20 carbon atom, preferably 10–18) materials such as long chain alkyl sulfates, long chain alkyl sulfonates, long chain alkyl phosphates, long chain alkyl ether sulfates, long chain alkyl alpha olefin sulfonates, long chain alkyl taurates, long chain alkyl isethionates (SCI), long chain alkyl glyceryl ether sulfonates (AGES), sulfosuccinates and the like. Those anionic surfactants can be alkoxylated, preferably ethoxylated, or not. The preferred anionic surfactants are the high foaming sulfates and sulfonates, particularly those which are ethoxylated such as sodium laureth (2 ethoxy) sulfate. All these materials are highly water soluble as the sodium, potassium, alkyl and ammonium or alkanol ammonium containing salt form and provide high foaming cleansing power. Since mildness is a clearly a desirable attribute, it is preferred to have little or no anionic surfactant which has a high irritation potential. For example, fatty acid carboxylate soaps are present in limited quantity or not present at all. When using surfactants such as sulfates or sulfonates, preferably ethoxylated, the composition generally has less than about 3wt %, more preferably no presence of an additional anionic surfactant.

The quantity of the anionic surfactant is not unduly significant; however, minimum quantities of at least about 2 wt. % of the composition should be employed. Very little benefit above about 25 wt. % of the composition is generally gained. Generally, a range of about 5 to about 20 wt. %, preferably about 7 to about 13 wt. % of the composition can be employed.

The second component of the cleansing phase is an amphoteric surfactant. These surfactants are generally known for their high surfactant activity, lather forming and mildness. Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminoipropane sulfonate, N-alkyltaurines, such as the one prepared by reacting dodecylamine with sodium isethionate according to the teaching of U.S. Pat. No. 2,658,072, N-higher alkyl aspartic acids, such as those produced according to the teaching of U.S. Pat. No. 2,438,091, and the products sold under the trade name "Miranol" and described in U.S. Pat. No. 2,528,378. Other amphoterics such as betaines are also useful in the present composition.

Examples of betaines useful herein include the high alkyl betaines such as coco dimethyl carboxymethyl betaine, lauryl dimethyl carboxy-methyl betaine, lauryl dimethyl alpha-carboxyethyl betaine, cetyl dimethyl carboxymethyl betaine, lauryl bis-(2-hydroxyethyl)carboxy methyl betaine, stearyl bix-(2-hydroxypropyl) carboxymethyl betaine, oleyl dimethyl gamma-carboxypropyl betaine, lauryl bix-(2-hydro-xypropyl) alpha-carboxyethyl betaine, etc. The sulfobetaines may be represented by coco dimethyl sulfopropyl betaine, stearyl dimethyl sulfopropyl betaine, amido betaines amidosulfobetaines, and the like. The betaines are generally preferred with the long chain alkyl group particularly coco, most preferred. Amido groups therein are also preferred. The most preferred betaines are the cocoamido propyl or ethyl betaines.

The quantity of amphoteric agent minimum is not unduly significant but should be at least 0.2 wt. % of the composition, preferably about 0.5 wt. %. However, the clarity of the aqueous phase must be maintained. The quantity of amphoteric reagent can affect the clarity. For example, with cocoamidpropylbetaine, a level not exceeding about 2 wt % can be employed. Generally there is no more than about 10 wt. %, assuming that clarity is maintained, preferably no more than about 7 wt. %.

A third component of the composition cleansing phase is not required but is preferred and is a nonionic, mild surfactant. Examples of such surfactants include EO-fatty alcohol, sorbitan and sorbitol esters, glucose ethers and alkylated polyglycosides amine oxides, alkanolamides (CDEA, CMEA) and the like. Preferred are alkanolamides and the alkylated polyglycosides (APG). The degrees of polymerization of the APG is preferably in a range of from about 1 to about 2, more preferably about 1.1 to about 1.6. The number of carbon atoms in the alkyl, preferably normal, range from about 8 to about 20 preferably about 10 to about 18. The alkanolamides have an alkyl group of the same length range as the APG alkyl. The APG can be alkoxylated, preferably ethoxylated, or left without ethoxylation. These materials are readily available from suppliers such as Emery, Henkel and Seppic.

The quantity of nonionic surfactant can vary substantially. Generally a minimum of about 0.5 wt % of the composition is employed. Above about 10 wt % generally does not achieve substantial benefits and merely adds cost. A range of about 0.75 to about 7 wt %, preferably about 1 to about 4 wt % can be employed.

From the nature of the invention, it is clear that any additional materials which may typically be present in aqueous compositions such as colorants, preservatives, chelating agents, fragrances and like can also be present in the composition as long as the clarity and stability of the system, as defined, can be maintained. The same criteria also applies to any additional "actives" such as surfactants with the additional proviso that the mildness of the system be preserved.

The matching of these two, preferably three components of the aqueous phase of the compositions brings about an excellent mix of properties for cleansing, such as high foam, long lasting controlled lather and a desirable mildness. Clarity is a significant characteristic of this phase and the clearness is maintained for lengthy periods of time. For example clarity of the finished composition has been maintained for a period of at least three (3) months at a temperature of 43° C. This clarity is measured by transmittance. It is measured directly on the end product (after removing the particles with a spoon) by measuring on a UV spectrophotometer at 600 nm. Acceptable transmittance is at least about 85%, preferably above about 90%. Of course, colorants, i.e. dyes, by their inherent nature absorb electromagnetic radiation in the measured range. Therefore, transmittance on the spectrophotometer is measured on the end product prior to adding the dye and/or the clarity evaluated visually.

The composition of the invention provides a unique method for delivering conditioning agents to the skin and hair. Within the clear aqueous phase are stably suspended particles which bear on and/or inside their surface conditioning agents. These conditioning agents include but are not limited to emollients, anti-oxidants, vitamins, oils, and any other oil like material applied to the skin or hair for conditioning effect. These particles have a density generally very close to that of water, 1 gm/cm$^3$, for ease of suspension and stability. A preferred density range is about 0.92 to about 1.05 gm/cm$^3$ more preferred, about 0.97 to about 1.02 gm/cm$^3$.

Their size should be such that they can bear the desired amount of conditioning agent and be readily physically degraded so that the conditioning agent can be delivered to the skin and hair. A further desired attribute of the particle is that it has optimal visual impact to the composition user. Generally the size of the particle can vary from about 200 to about 2500 micron. Preferably the particle size is about 400 to about 2000 micron and even more preferably about 800 to about 1800 micron and most preferably about 1000 to 1500 microns. The material comprising the particle should be compatible with water and the skin or hair. Generally such materials can include gelatins, arabic gums, collagens, polypeptides from vegetable or animal origin, alginates, polyamides, glycosamino glycans, mucopolysaccharides, ethylcellulose and the like. Through coacervation, multicoating protein deposition, or reticulation technologies microcapsules can be formed which enclose the oil like conditioning agents. The conditioning agents can be applied to the particle surfaces by impregnation.

When applied to the skin or hair during normal cleansing procedures, these particles are abraded, released and deposit their contents on the skin or hair. Examples of "oily" materials which can be within the microcapsule are vitamins, provitamins; mineral oils, vegetable oils, emollients such as fatty esters and silicones, oil soluble vegetable extracts or animal extracts and the like. These oil bearing particles are available from Hallcrest Liquid Crystal Technology Ltd a UK company having offices in Glenview, Ill., U.S.A. and from LIPO Chemicals. Other materials which can be employed are oil impregnated particles available as Elespheres® from Laboratories Serobiologiques, France. Also collagen spheres and glucose amino glycans "GAG" spheres from Coletica (France) called Collaspheres or Thalaspheres. The preferred particles are the microcapsules from Hallcrest, most preferably the green, silver and iridescent colors. The particles plus the conditioning agents borne thereon are generally from about 0.02 to about 1.2wt % of the composition, preferably about 0.05 to 0.75 wt %. An effective mount of conditioning agent should be carried by the particles. Generally, at least about 40% of the loaded particle is conditioning agent, preferably at least about 60 wt. % of the particle. One of the loaded particles from Coletica of France is about 98 wt. % conditioning agent.

The last essential component of the composition and the one which provides the stable suspension of particles is the xantham gum. These materials are, in general, hydrophilic colloids made up of a polymer backbone of β-1, 4-linked D-glucose residues. A trisaccharide branch contains one glucoronic acid unit between two mannose units and is linked to every other glucose unit at the number 3 position. The xantham gum has a light transmission of at least about 85% when measured as a 1 wt. % solution in distilled water using a UV spectropholometer such as a Pye Unicam at 600 nm. Distilled water is used as a 100% transmission standard. Preferred transmission is at least about 90%. Xantham gums with lower transparency, that is about 70% transmission, did not provide compositions which maintained clarity over time. This characteristic preferably coupled with the xantham gum particle size, appear to be significant to the preparation of a clear and stable composition. The particle sizes of the preferred xantham gums are such that 100% goes through 60 mesh (250 micron) and at least 95% through 80 mesh (180 micron) and preferably at least 99% through 177 micron and more preferably at least 92% through 200 mesh (80 micron). Other xantham gums were evaluated and were able to provide a stable suspension of the oil bearing particles but brought cloudiness to the aqueous phase. Other materials were tried but failed for various reasons. For example, carrageenan gum brought about a lack of clarity in the aqueous phase. Various Carbomers containing crosslinked acrylic acid homopolymers brought about a lack of clarity and did not provide an elastic structure build-up. Various organo clays had similar problems as the Carbomers. Carboxy methyl cellulose had no elastic behavior in the system. Without the proper elastic behavior the particles are not stably suspended.

The successful suspending system should also provide the desired viscosity. The composition is to be liquid, pourable and in non gellular or gellular form. It can be delivered from a hand pumpable container or poured. Generally the desired viscosity is from about 1000 to 8000 centipoises as measured on a Brookfield RVTD viscometer spindle 5 at 10 rpm and 25° C., preferably about 1200 to about 4500 centipoises. Suitable xantham gums are available from Kelco located in Brussels, Belgium and marketed as Keltrol T or Keltrol TF, preferably Ketrol T. The xanthan gum should be present in from about 0.3 to about 1 wt % of the composition, preferably about 05 to 0.95%, most preferably about 0.7 to 0.85 wt %. If xantham gum above about 1 wt. % of the composition is employed, the composition can become cloudy and/or have unacceptable skin feel such as stickiness or sliminess; however, in general, quantities of xanthan gum below about 1.1 wt. % can perform in an acceptable manner, for example, 1.05 wt. %.

The compositions of the invention are prepared by standard techniques taking into account the specific requirements of the composition. The xantham gum employed is wet into a solubilized fragrance, assuming a fragrance is to be used. When a fragrance is employed, it is preferred to use a perfume solubilizer of PEG-9 tridecylether and PEG-40 hydrogenated castor oil. This combination is then added to the water of the composition using a high shear homogenizer, thereby providing clarity and viscoelasticity to the composition. The various surfactants are then added followed by the conditioning bearing particles. The proper viscosity and suspension is achieved. The preferred pH is slightly acidic and more preferably ranges from about 5.2 to about 5.8 so as to assist in maintaining proper compatibility with the skin. After optional material(s) are added, the balance of the composition is water.

Aging studies were conducted so as to measure both the clarity (clearness) of the aqueous phase and the stability of the suspended particles. In order to be considered clear, the composition should show at least 85% transmittance as measured on the product as it is after removal of particles, at 600 nm by a UV spectrophotometer. The transmission standard is the water used in the composition. A stable suspension was determined to be no visual settling together of particle at the bottom of the container, no visual rising of the particles to the top, no significant alteration of the particle positions in the container and no observed physical change of the particles such as in shape or color which would indicate an interaction with their environment. The time period was at least three (3) months at 43° C. No modification of foam performance profile of the finished product should be significantly present in that time period. This is an indication that the oily contents of the solid particles are not released.

Below are examples of the invention demonstrating the uniqueness of the formulation with respect to its components, particularly the viscoelastic suspending agent and the conditioning agent bearing particles. These examples of the invention are intended to exemplify the invention and not be undue limitation(s) thereof.

| Example | Active wt %      | | | Xantham Gum[d] | Filled beads |
|---------|------|------|------|------|-------|
|         | SLES[a] | CAPB[b] | APG[c] |  |  |
| 1 | 8.2 | 2 | 1.25 | 0.8 | 0.45[e] |
| 2 | 8.2 | 2 | 0 | 0.8 | 0.5[e] |
| 3 | 8.2 | 2 | 0 | 0.8 | 0.75[f] |

[a]sodium laureth sulfate, 2EO
[b]cocoamidopropy betaine
[c]dodecyl polyglycoside, dp of 1.4.
[d]Keltrol T
[e]Hallcrest Type HC626
[f]Lab Serobiol. Elespheres BL 1000

Also present in each of the examples was an emulsified fragrance at 2 wt. % and 0.3 wt. % of a preservative. The balance was deionized water. In actual practice either tap or deionized water can be employed, preferably deionized.

After three months at 43° C., the compositions remained clear, at least 85% transmittance by UV spectrophotometer at 600 nm, after mechanical removal of particles, as measured against water. The particles remained stable as measured visually by no grouping together at the top or bottom as well as change of physical shape. No discoloring of the aqueous phase nor of the particles was observed after three months at 43° C. There appeared to be no effect on lathering at the end of the aging period of three months.

I claim:

1. A combination cleansing, conditioning composition comprising a stable, clear, aqueous cleansing phase having stably dispersed and suspended therein particles having an average diameter size of from about 400 to about 2000 microns bearing the conditioning agent, the aqueous cleansing phase remaining clear for a period of at least three months at 43° C. comprising:

a. at least about 2 wt. % of a high foaming anionic surfactant, b. an amphoteric surfactant in quantities of at least 0.2 wt. % of the composition wherein clarity of the aqueous phase is maintained, c. about 0.3 to below about 1.1 wt. % of a viscoelasticity enhancing suspending composition component comprised of a xanthan gum having an initial transmittance in a 1 wt. % distilled water solution of at least 85% as measured by a UV spectrophotometer at 600 nm, and d. the said particles, insoluble and stably suspended in the aqueous phase, bearing an effective conditioning amount of oily water insoluble or essentially water insoluble skin or hair conditioning agents, the particles being of such a material to readily deliver the conditioning agent to the skin or hair when the particle is abraded against the skin or hair during ordinary cleansing activities.

2. The composition in accordance with claim 1 wherein a is an ethoxylated sulfate or sulfonate.

3. The composition in accordance with claim 1 wherein b is a betaine.

4. The composition in accordance with claim 1 wherein a nonionic surfactant is also present.

5. The composition in accordance with claim 1 wherein the xantham gum has (a) a particle size such that 100% goes through a 250 micron mesh screen.

6. The composition in accordance with claim 1 wherein the particles bear the oily conditioning agent within or upon the surface of the particle.

7. The composition in accordance with claim 2 wherein the sulfate or sulfonate is about 2 wt. % to about 20 wt % of the composition.

8. The composition in accordance with claim 3 wherein the betaine is at least 0.2 but less than about 2 wt % of the composition.

9. The composition in accordance with claim 4 wherein the nonionic surfactant is an alkylated polyglycoside and is from about 0.5 wt. % to about 10 wt % of the composition.

10. The composition in accordance with claim 5 wherein the xantham gum is from about 0.6 wt. % to about 0.95 wt % of the composition.

11. The composition in accordance with claim 6 wherein the particle have an average diameter size of from about 800 to about 1800 microns.

12. The composition in accordance with claim 1 wherein oily conditioning agents are selected from the group consisting of vitamins, provitamins, emollients, moisturizers, silicones, vegetable oils and mineral oils.

13. The composition in accordance with claim 8 wherein the betaine is cocoamidopropyl betaine.

14. A method of concomitantly cleansing and conditioning the skin or hair which comprises applying the composition of claim 1 to the skin or hair.

* * * * *